(12) United States Patent
Miyakawa et al.

(10) Patent No.: US 7,245,366 B2
(45) Date of Patent: Jul. 17, 2007

(54) SURFACE INSPECTION METHOD AND SURFACE INSPECTION APPARATUS

(75) Inventors: Kazuhiro Miyakawa, Tokyo (JP); Yoichiro Iwa, Tokyo (JP); Akihiko Sekine, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 430 days.

(21) Appl. No.: 10/864,062

(22) Filed: Jun. 9, 2004

(65) Prior Publication Data
US 2004/0252295 A1 Dec. 16, 2004

(30) Foreign Application Priority Data
Jun. 10, 2003 (JP) .............. 2003-165458

(51) Int. Cl.
*G01N 21/00* (2006.01)
(52) U.S. Cl. .............. 356/237.2; 356/237.3; 356/237.4
(58) Field of Classification Search .............. 250/234; 356/237.1–237.5
See application file for complete search history.

(56) References Cited

U.S. PATENT DOCUMENTS

| | | | | |
|---|---|---|---|---|
| 5,426,506 A | * | 6/1995 | Ellingson et al. ........... 356/369 |
| 5,471,066 A | * | 11/1995 | Hagiwara ............... 250/559.48 |
| 5,644,392 A | * | 7/1997 | Soest et al. .............. 356/237.1 |
| 5,982,482 A | * | 11/1999 | Nelson et al. ........... 356/237.1 |
| 6,064,477 A | * | 5/2000 | Matsumoto et al. ..... 356/237.2 |
| 6,081,325 A | * | 6/2000 | Leslie et al. .............. 356/237.2 |
| 6,104,481 A | * | 8/2000 | Sekine et al. ............. 356/237.5 |
| 6,204,918 B1 | * | 3/2001 | Isozaki et al. ........... 356/239.8 |
| 6,292,260 B1 | * | 9/2001 | Lin et al. .................. 356/237.4 |
| 6,483,735 B1 | * | 11/2002 | Rentzepis .................... 365/119 |
| 6,538,730 B2 | * | 3/2003 | Vaez-Iravani et al. ... 356/237.2 |
| 6,603,542 B1 | * | 8/2003 | Chase et al. .............. 356/237.4 |
| 6,621,570 B1 | * | 9/2003 | Danko ...................... 356/237.4 |
| 6,633,384 B1 | * | 10/2003 | Drake et al. ................. 356/432 |
| 7,002,677 B2 | * | 2/2006 | Bevis et al. .............. 356/237.5 |

FOREIGN PATENT DOCUMENTS

| | | |
|---|---|---|
| JP | 56-067739 | 6/1981 |
| JP | 62-261045 | 11/1987 |

* cited by examiner

*Primary Examiner*—Layla G. Lauchman
*Assistant Examiner*—Jarreas C. Underwood
(74) *Attorney, Agent, or Firm*—Chapman and Cutler LLP

(57) ABSTRACT

A surface inspection apparatus includes an LD (10 for emitting a laser beam (L0), an irradiation optical system for entering the emitted laser beam (L0) onto an inspection surface (210) of a wafer at predetermined depression angle ($\alpha$), a scanning device (30) to displace the wafer (200) in order for the laser beam (L0) scans the inspection surface (210) in a spiral, an light intensity detecting device (50) to detect light intensity, and a scattered light detecting optical system (40) for guiding scattered light (L2) emitted from an irradiation area (220) in which the laser beam (L0) is entered. The light intensity detecting device (50) includes a multianode PMT (51) for detecting the light intensity by decomposing the scattered light (L2) into 10 channels (ch) in a one-dimensional direction (Y axis direction).

12 Claims, 7 Drawing Sheets

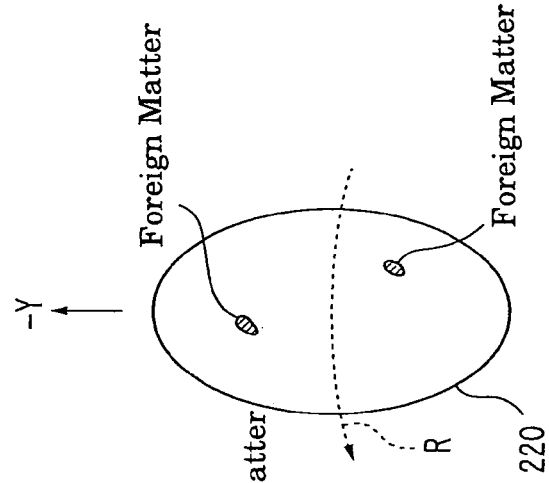
FIG. 4A
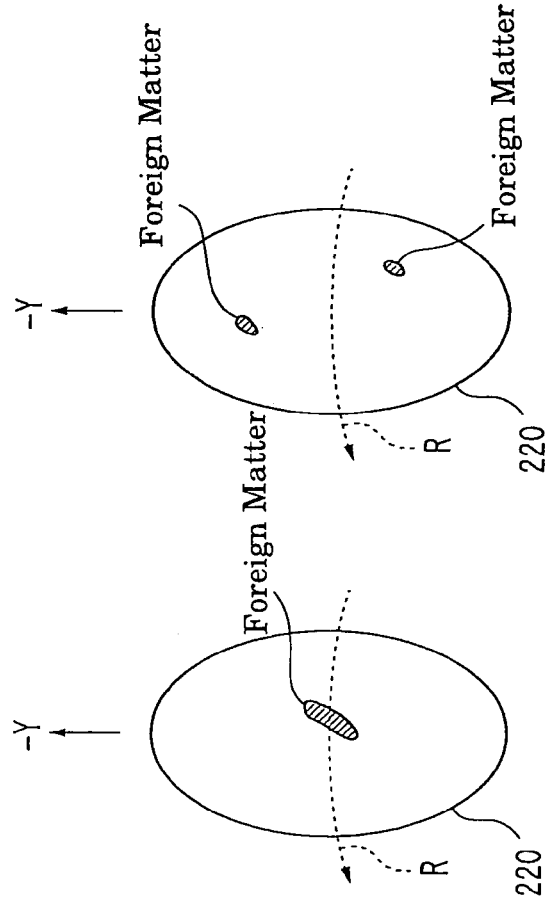
FIG. 4B
FIG. 4C
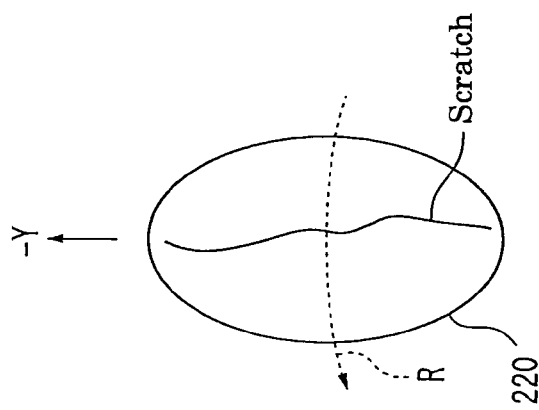
FIG. 4D
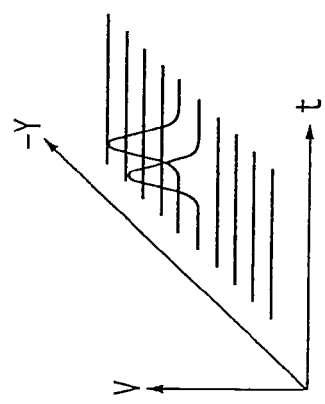
FIG. 4E
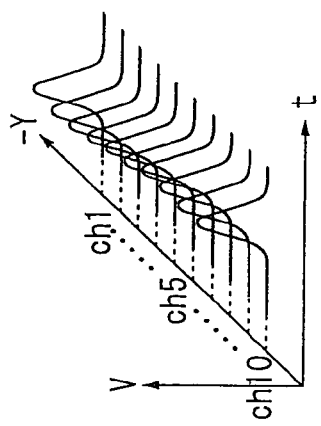
FIG. 4F

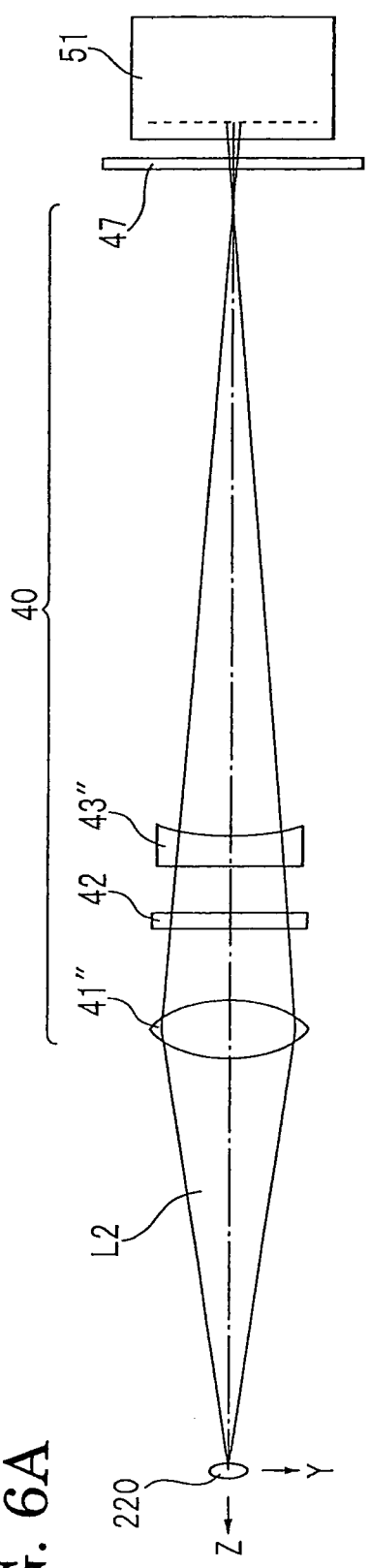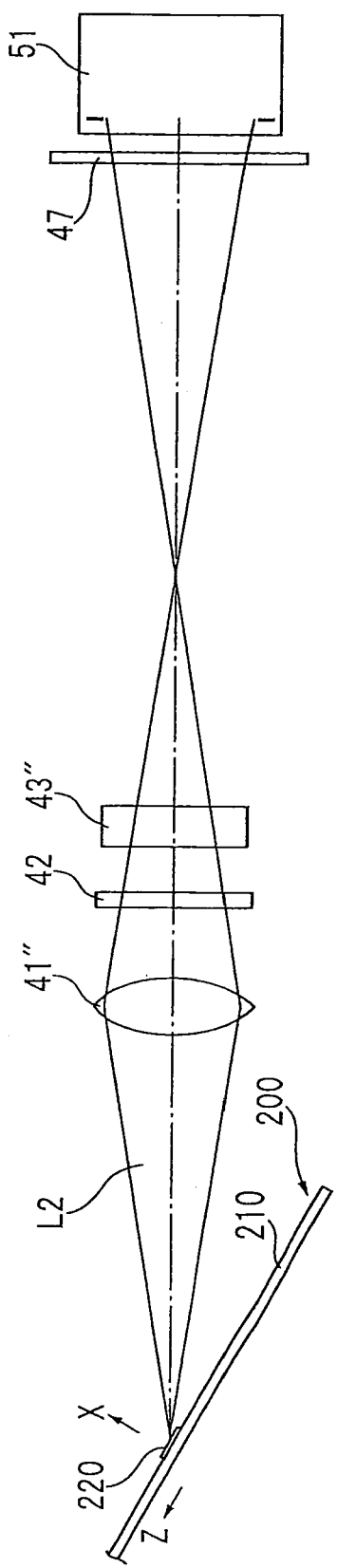

SURFACE INSPECTION METHOD AND SURFACE INSPECTION APPARATUS

FIELD OF THE INVENTION

The present invention relates to a surface inspection apparatus, more particularly the invention relates to an improvement in a method and an apparatus for inspecting a defect on a surface to be inspected by irradiating a luminous flux on the surface to be inspected and detecting the intensity of scattered light.

RELATED ART STATMENT

There has been conventionally know a surface inspection apparatus for inspecting a defect of an inspection surface, such as a foreign matter or scratches (including a crystal defect) adhered to a surface (inspection surface) of an inspection object such as a semiconductor wafer, for example.

The surface inspection apparatus, for example, comprises a light source for emitting a predetermined luminous flux such as a laser beam, an irradiation optical system for irradiating the luminous flux emitted from the light source on the surface to be inspected at a predetermined irradiation angle, a scanning device for displacing the inspection object in order for the luminous flux to scan the inspection surface, a light intensity detecting device for detecting the irradiated light intensity, and a scattered light detecting optical system for guiding the scattered light emitted from the inspection surface area (irradiation area) in which the luminous flux is projected to the light intensity detecting device. The surface inspection apparatus inspects the defect depending upon the intensity of the scattered light inspected by the light intensity detecting device (See JP-A-S56-67739).

Here, the scattered light from the irradiation area means light scattering in the direction other than the direction in which the luminous flux projected on the inspection surface regularly reflects in the irradiation area.

Therefore, in the scattered light detecting optical system, the optical axis is set in the direction other than the regular reflection direction, and the optical axis is set to be directed to the irradiation area at a predetermined depression angle with respect to the inspection surface, for example.

The above conventional surface inspection apparatus can detect the presence and absence of the defect, however, the apparatus cannot discriminate a single large defect or a plurality of small defects.

More specifically, the surface inspection apparatus detects the intensity of scattered light emitted from the irradiation and the whole irradiation area as a single unit, and judges the presence and absence of the defect based on the detected intensity. The apparatus, accordingly, cannot judge whether or not a plurality of small defects is existed in the irradiation area, or whether or not the single large defect is existed in the irradiation area. The intensity to be defected may change in accordance with the depth or the height of the defect having the inspection surface as a reference. It may be considered that the intensity detected by the single small defect becomes greater than the intensity detected by the large defect.

SUMMARY OF THE INVENTION

The present invention has been made in view of aforementioned problem. It is an object of the present invention to provide a surface inspection method and a surface inspection apparatus capable of easily discriminating a plurality of small defects or a single large defect with respect to a defect detected in an irradiation area of an inspection surface.

In order to solve the above problem, in the surface inspection method and the surface inspection apparatus according to the present invention, a spatial resolution in an irradiation area is improved by decomposing intensity of scattered light into a plurality of channels in a predetermined one-dimensional direction and by detecting the light intensity.

More particularly, the surface inspection method for conducting an inspection of an inspection surface by entering a predetermined luminous flux with respect to the inspection surface of an inspection object as a surface inspection object at a predetermined incident angle, and by relatively displacing at least any one of said luminous flux and said inspection object such that said luminous flux scans said inspection surface, and by detecting an intensity of a scattered light reflected by a portion of said inspection surface in which said luminous flux is entered, comprises the steps of decomposing said scattered light into a plurality of channels in a one-dimensional direction corresponding to a predetermined direction in the portion of the inspection surface in which the luminous flux is entered, and respectively detecting a light intensity of each decomposed scattered light which is obtained by decomposing said scattered light.

Here, a semiconductor wafer, various boards, etc. are included as a typical inspection object. However, the inspection object is not limited to those objects, and it can be any object to be a subject conducting the surface inspection by detecting the presence of a foreign matter adhered onto the inspection surface and a scratch formed on to the inspection surface or the position of those defects.

It is also preferable to apply a laser beam having high coherence as the luminous flux to be entered onto the inspection surface.

When the scattered light is spatially decomposed into a plurality of channels corresponding to a predetermined direction in the irradiation area in which the luminous flux is entered, each decomposed scattered light which is obtained by decomposing the scattered light becomes the scattered light respectively emitted from each divided portion in which the irradiation area is divided in a predetermined direction.

Consequently, the scattered light intensity for a position in the irradiation area (position corresponding to a predetermined direction) can be detected by respectively detecting the light intensity of each decomposed scattered light, so that the detecting resolution (spatial resolution) of the position on which the scattering is generated, i.e. the defect position of the surface can be improved.

It is also possible to distinguish between a plurality of separated small defect and a consecutive large defect by sequentially comparing each of the detecting intensity by a plurality of channels arranged in the one-dimensional direction between adjacent channels.

More particularly, when the light intensity of a predetermined level or higher is detected by a channel, and the light intensity of the substantially same level is detected in the channels adjacent to the channel, and then a number of channels by which such light intensity is detected is continued, the light intensity can be determined that a large defect (such as a scratch) extending in a predetermined direction in the irradiation area corresponding to the arrangement direction (the one-dimensional direction) of the channel is presented. On the other hand, although the light intensity of a predetermined level or higher is detected by a channel, if the light intensity detected in the channels adjacent to the channel is light intensity indicating a significant difference from a predetermined level, or although the light intensity of the substantially same level is detected in adjacent channels, if the channels detected such light intensity are continued only for 2 or 3 channels, the defect is not a defect continued in a predetermined direction within the irradiation area, and the defect is determined as a small defect (such as adhesion of a foreign matter).

As a result, the adhesion of a plurality of small foreign matters (projections with respect to a surface) and a long scratch (a concave with respect to a surface), which were difficult to be distinguished, can be easily distinguished.

Moreover, at least in a one-dimensional direction means that the light intensity of the scattered light is detected by not only decomposing the scattered light into a plurality of channels in the one-dimensional direction of the inclined plane, but also decomposing the scattered light into a plurality of channels in the orthogonal direction (in the inclined plane) orthogonal to the one-dimensional direction, i.e. decomposing into the two-dimensional matrix.

When the detection is carried out by decomposing into the two-dimensional matrix, the detection resolution of the position where the scattering is generated, i.e. the defect potion in the irradiation area can be further improved, and also a plurality of separated small defects, a consecutive long and thin defect, and a defect extending over the surface can be distinguished by sequentially comparing each detecting intensity by a plurality of channels arranged in the two-dimensional direction between adjacent channels of right and left and up and down.

When the defect is a consecutive long and thin defect, it is possible to determine the extending direction.

It is preferable for the detection of the scattered light emitted from the irradiation area to be detected from the direction substantially orthogonal to the direction projecting the advancing direction of the incidence luminous flux onto the inspection surface, for example, and i is the direction oriented to the irradiation area at a predetermined depression angle with respect to the inspection surface.

The scattered light which is detected at this point is so-called side scatter, because the side scatter can be distinctively detected as the scattered light compared to forward scatter detected in a downstream side of the incidence luminous flux over the side scatter (direction forming an acute-angled angle with respect to the direction projecting the advancing direction of the incidence luminous flux onto the inspection surface) or a back scatter detected in an upstream side of the incidence luminous flux over the side scatter (direction forming an obtuse angle with respect to the direction projecting the advancing direction of the incidence luminous flux onto the inspection surface).

Here, a predetermined angular direction with respect to a minor axis direction means a direction forming an angle other than 0 degree with respect to the minor axis direction. Therefore, a predetermined angular direction includes an oblique direction, which is inclined with respect to the major axis direction and the minor axis direction, and the major axis direction.

According to the surface inspection device of the present invention, the surface inspection device comprises a light source for emitting a predetermined luminous flux, an irradiation optical system for entering the luminous flux emitted from the light source with respect to an inspection surface of an inspection object as a surface inspection object at a predetermined incident angle, a scanning device to relatively displace at least any one of the luminous flux and the inspection object such that the luminous flux scans the inspection surface, a light intensity detecting device to detect an intensity of an entered light, and a scattered light detecting optical system for guiding a scattered light emitted from a portion of the inspection surface in which the luminous flux is entered, wherein the light intensity detecting device is set to decompose the scattered light into a plurality of channels at least in a one-dimensional direction on an inclined plane of the light intensity detecting device and to detect the light intensity.

Here, a semiconductor wafer, various boards, etc. are included as a typical inspection object. However, the inspection object is not limited to those objects, and it can be any object to be a subject conducting the surface inspection by detecting the presence of a foreign matter adhered onto the inspection surface and a scratch formed onto the inspection surface, or the position of those defects.

It is preferable for the light source to apply a laser light source (semiconductor laser light source (LD), argon ion laser light source, etc.) emitting a laser beam having coherence as the luminous flux.

An optical axis of the scattered light detecting optical system should be set to condense at least a part of the scattered light other than the regular reflection light emitted form the irradiation area. For example, the optical axis of the scattered light detecting optical system can be set to condense the scattered light scatting in the direction substantially orthogonal to the advancing direction of the incidence luminous flux when projecting the incidence luminance flux entering on the inspection surface.

At this point, in order to effectively condense the scattered light from the portion of the inspection surface (irradiation area) in which the luminous flux is entered, it is preferable that the optical axis of the scattered light detecting optical system is set to direct the irradiation area at a predetermined depression angle with respect to the inspection surface. The scattered light, which is detected at this point, is so-called side scatter.

Since the one-dimensional direction on the inclined plane of the light intensity detecting device corresponds to a predetermined direction on the portion (irradiation area) of the inspection surface in which the luminous flux is entered, and if the scattered light is decomposed into a plurality of channels in the one-dimensional direction, each decomposed scattered light, which is obtained by decomposing the scattered light, becomes the scattered light respectively emitted from each divided portion divided into the predetermined direction of the irradiation area.

Therefore, the scattered light intensity for each position (position corresponding to a predetermined direction) on the irradiation area in which the luminous flux is entered can be detected by respectively detecting the light intensity of each decomposed scattered light, so that the detecting resolution where the scattering is generated, i.e. the defect position of the surface can be improved.

It is also possible to distinguish whether the defect is a plurality of separated small defects or a consecutive large defect by sequentially comparing each of the detecting intensity by a plurality of channels arranged in the one-dimensional direction between adjacent channels.

More particularly, when the light intensity of a predetermined level or higher is detected by a channel, and the light intensity of the substantially same level is detected in the channels adjacent to the channel, and then a number of channels by which such light intensity is detected is continued, the light intensity can be determined that a large defect (such as a scratch) extending in a predetermined direction in the irradiation area corresponding to the arrangement direction (the one-dimensional direction) of the channel is presented. On the other hand, although the light intensity of a predetermined level or higher is detected by a channel, if the light intensity detected in the channels adjacent to the channel is light intensity indicating a significant difference from a predetermined level, or although the light intensity of the substantially same level is detected in adjacent channels, if the channels detected such light intensity are continued only for 2 or 3 channels, the defect is not a defect continued in a predetermined direction within the irradiation area, and the defect is determined as a small defect (such as adhesion of a foreign matter).

As a result, the adhesion of a plurality of small foreign matters (projections with respect to a surface) and a long scratch (a concave with respect to a surface), which were difficult to be distinguished, can be easily distinguished.

Multianode Photomultiplier Tube (PMT), etc. are used as typical examples of the light intensity detecting device which is set to decompose the entered scattered light into a plurality of channels in the one-dimensional direction and to detect the light intensity. However, the light intensity detecting device is not limited to such multianode PMT, it may be a structure that a plurality of light detectors of multi-channel type and light detectors of single channel type are disposed corresponding to each channel.

Moreover, at least in a one-dimensional direction means that the light intensity of the scattered light is detected by not only decomposing the scattered light into a plurality of channels in the one-dimensional direction of the inclined plane, but also decomposing the scattered light into a plurality of channels in the orthogonal direction (in the inclined plane) orthogonal to the one-dimensional direction, i.e. decomposing into the two-dimensional matrix.

In case of applying the light intensity detecting device to detect the light intensity by decomposing the scattered light into the two-dimensional matrix, the detecting resolution where the scattering is generated, i.e. the defect position in the irradiation area can be further improved, and it is also possible to distinguish whether the defect is a plurality of separated small defect, a consecutive long and thin defect, or a defect extending to a surface by sequentially comparing each detecting intensity by a plurality of channels arranged in the two-dimension between adjacent channels of right and left and up and down.

When the defect is a consecutive long and thin defect, it is possible to determine the extending direction.

However, for a quality of a normal product (inspection object), the inspection quality can be sufficiently improved by the surface inspection apparatus including the light intensity detecting device which is set to detect the light intensity by decomposing the scattered light into a plurality of channels only in the one-dimensional direction. Therefore, it is preferable to decompose the scattered light in the one-dimensional direction in terms of the balance between the manufacturing cost and the inspection quality of the surface inspection device.

BRIEF DESCRIPTION OF THE DRAWINGS

FIGS. 4A, 4B, 4C, 4D, 4E, and 4F are views illustrating the correspondence between a type and a state of defect (FIGS. 4A, 4B, and 4C) and detecting light intensity (FIGS. 4D, 4E, and 4F).

FIG. 5A is a plan view corresponding to FIG. 2A; FIG. 5B is a side view corresponding to FIG. 2B.

FIGS. 6A, 6B show another embodiment (modification example 2) of the scattered light detecting optical system; FIG. 6A shows a plan view corresponding to FIG. 2A; FIG. 6B shows a side view corresponding to FIG. 2B.

DESCRIPTION OF THE PREFERRED EMBODIMENTS

Hereinafter, embodiments of a surface inspection method and a surface inspection apparatus according to the present invention will be described with reference to the drawings.

First Embodiment

Figure 1:
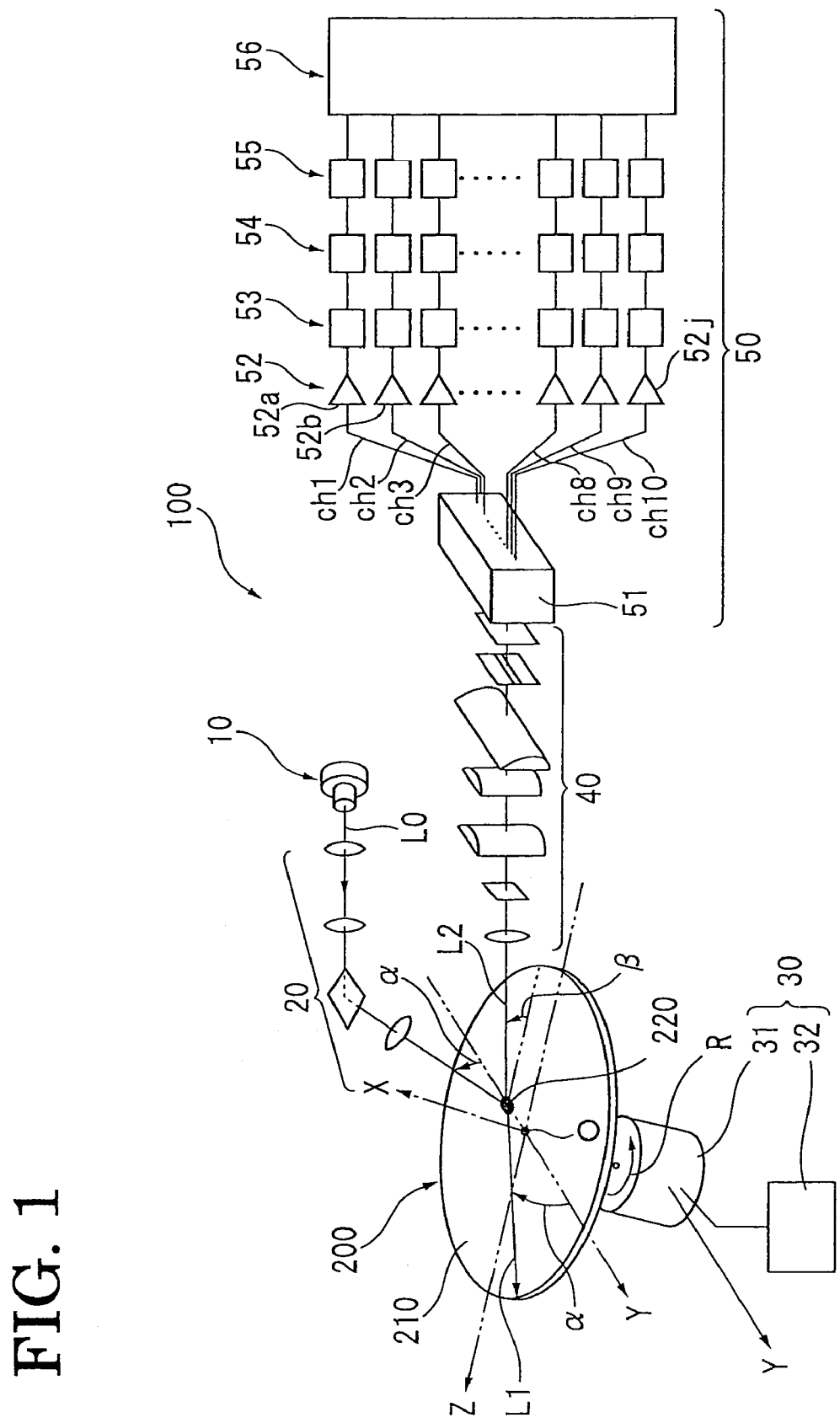
FIG. 1 is a schematic block diagram illustrating a surface inspection apparatus according to an embodiment of the present invention.

FIG. 1 illustrates a surface inspection apparatus according to a first embodiment of the present invention.

The surface inspection apparatus 100 comprises a semiconductor laser light source (hereinafter referred to as LD) for emitting a laser beam L0, an irradiation optical system 20 for projecting the laser beam L0 emitted from the LD 10 onto an inspection surface 210 of a wafer (inspection object) 200 of a substantially true circular board at a predetermined depression angle $\alpha$ (=incident angle ($90°-\alpha$)), a scanning device for displacing the wafer 200 such that the laser beam L0 scans the inspection surface 210 in spiral (See FIG. 2A), a light intensity detecting device 50 for detecting the intensity of the incident light, and a scattered light detecting optical system 40 for guiding a scattered light L2 reflected by a portion (hereinafter referred to as irradiation area) of the inspection surface 210 in which the laser beam L0 is entered, to the light intensity detecting device 50.

Here, the light intensity detecting device 50 is set that the scattered light L2 is decomposed into 10 channels (ch) in a one-dimensional direction (Y axis direction) of the incident plane of the light intensity detecting device 50, and the decomposed 10 channels are detected, as described later.

If the orthogonal axis in the inspection surface 210 of the wafer 200 is adopted as a Y axis and a Z axis, and the axis orthogonal to the inspection surface 210 is adopted as an X axis, the inspection surface 210 is kept with an inclined state which is slightly turned about the Y axis of the horizontal axis. The X axis is hereby inclined with respect to the vertical axis of the horizontal plane (See FIG. 1 and FIG. 2B).

The laser beam L0 emitted from the LD10 is guided in the XY surfaces to the irradiation area 220 by the irradiation optical system 20. If the laser beam L0 is projected on the inspection surface 210 along the X axis, the projection locus overlaps with the Y axis. In the plan view shown in FIG. 2A, the projection locus becomes the locus along the vertical axis of the horizontal plane, so that the projection locus of the laser beam L0 onto the inspection surface 210 does not overlap with the Y axis.

The reflection light L1 of the laser beam L0 which is regularly reflected by the irradiation area 220 emits from the irradiation area 220 at an elevation angle α (reflection angle (90°−α)).

The irradiation area 220 of a laser spot formed on the inspection surface by the incidence of the laser beam L0 on the inspection surface 210 is a substantially elliptical shape having a major axis in the Y axis direction.

The scanning device 30 comprises a turning stage (turning device) 31 for turning the wafer 200 about the center O as the turning center (X axis) and a liner motor (liner movement device) 32 for linearly moving the wafer 200 together with the turning stage 31 in the Y axis.

The laser beam L0 scans the wafer 200 in spiral while turning the wafer 200 by the turning stage 31 and linearly displacing the wafer 200 by the liner motor 32.

The optical axis O2 of the scattered light detecting optical system 40 is substantially orthogonal to the Y axis. The scattered light detecting optical system 40 is directed to the irradiation area 220, and is disposed at a depression angle β (in this embodiment β=30°) with respect to the inspection surface 210. The scattered light detecting optical system 40 converges the scattered light L2 scattering in the direction other than reflection light L1 reflected by the irradiation area, and guides the converged scattered light L2 to the light intensity detecting device 50.

In order of the upstream side in the advancing direction of the scattered light L2, the scattered light detecting optical system 40 comprises a condenser lens 41 for converging the scattered light L2 emitted from the irradiation area 220, a polarizing plate 42 for adjusting the wave surface of the entered scattered light L2, cylindrical lenses 43, 44 without having power to the vertical direction component of the scattered light L2 and having positive power only with respect to the Y axis direction component of the scattered light L2, a cylindrical lens 45 without having power with respect to the Y axis direction component and having positive power with respect to the vertical direction component, a field stop 46 for narrowing down the divergence of the scattered light L2 to the size of the inclined plane of the light intensity detecting device 50, and an ND filter 47, as shown in FIG. 2.

By the magnification differences between the power in the Y axis direction and the power in the vertical direction with the above mentioned three cylindrical lens 42, 43, and 44, the imaging magnification in the Y axis direction is about 70 times, and the imaging magnification in the vertical direction is about equal (one time). For example, when the major axis along the Y axis direction of the irradiation area 220 is 0.14 mm, the opening length along the Y axis direction of the field stop 46 is set to 9.8 mm (=0.14×70).

The position in which the field stop 46 is disposed is a conjugate position in the Y axis direction and the vertical direction of the scattered light detecting optical system 40.

In this embodiment, the focal length and the numerical aperture of the condenser lens 41 is set to f=21 mm and NA=0.3, the focal length of the cylindrical lens 43 is set to f=210 mm, and the focal length of the both cylindrical lenses 44, 45 is respectively set to f=21 mm.

In each of the views, a light track, a curvature of lens, a distance between lenses, and the like are schematically displayed, so that the focal length f of each of the above described lenses 41, 43 to 45 is not preciously displayed.

The cylindrical lenses 43, 44 comprise so called a telecentric optical system, and the image of the scattered light emitted from the irradiation area 220 is focused onto the position P.

The light intensity detecting device 50 decomposes the entered scattered light L2 into the 10 channels (ch) arranged along the Y axis direction. The light intensity detecting device 50 comprises a multianode PMT 51 for detecting the light intensity of the decomposed each channel ch1 to ch10, ten amplifiers (from an amplifier 52a corresponding to ch1 to an amplifier 52j corresponding to ch10) for respectively amplifying the signal indicating the light intensity output from each channel ch1, ten BPFs (band pass filter) 53 for respectively eliminating a predetermined noise component from the signal amplified by each amplifier 52, and ten A/D converters 54 for respectively converting the signal passing each BPF 53 into a digital signal, ten memories 55 for respectively storing the digital signal digitized by each A/D converter 54, and an analysis device 56 for determining a size, type, and the like of a defect on the inspection surface 210 in the irradiation area 220 based on the digital signal according to the light intensity for each channel stored in each memory 55.

Figure 3:
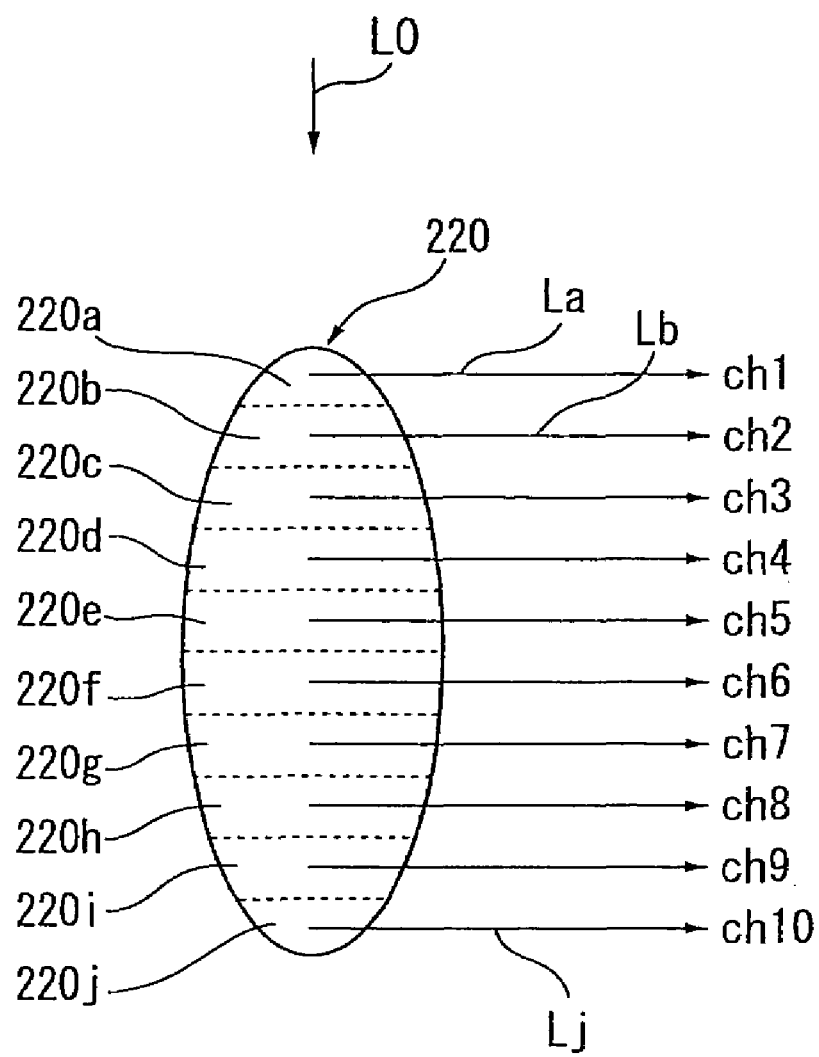
FIG. 3 is a view showing the correspondence between the divided areas of the irradiation area and the channels decomposed by the multianode PMT.

Here, the ten channels ch1 to ch10 of the multianode PMT 51 correspond to ten areas 220a to 220j divided along the Y axis direction of the irradiation area 220 as illustrated in FIG. 3 by the relationship with the scattered light detecting optical system 40. The scattered light La (shown by solid line) emitted from the first area 220a is entered to the ch1, the scattered light Lb emitted from the second area 220b is entered to ch2, and the scattered light Lj (shown by dotted line) emitted from the tenth area 220j is entered to the ch10.

Instead of including the analysis device 56, the light intensity detecting device may be configured to have a displaying device for displaying the digital signal according to the light intensity for each channel stored in each memory 55 as a graph or a digital signal for each channel, for example. The light intensity detecting device may also be constituted to include a printer or a plotter which prints the digital signal according to the light intensity for each channel as a graph or prints as a digital numerical value.

The cylindrical lenses 43, 44 comprises a telecentric optical system, so that the principle ray of each La to Lj which is emitted from each area 220a to 220j and passed the cylindrical lens 43 is parallel to the optical axis O2.

In the surface inspection device 100 comprising the light intensity detecting device 50 having the display device, the printer, and the like other than the analysis device 56, the determination such as a defect size and a defect type of the inspection surface 210 in the irradiation area 220 can be determined by an analyst which observed the output information based on the information displayed on the display device or the information printed on a media such as a paper.

The analysis device 56 may be configured to include the above described display device and the printer.

Next, functions of the surface inspection device 100 according to the present invention will be explained.

First, the laser beam L0 is emitted from the LD10, and the emitted laser beam L0 is projected adjacent to the center O on the Y axis in the inspection surface 210 of the wafer 200 at a depression angle α from the negative direction of the Y axis by the irradiation optical system 20.

Here, the oval irradiation area 220 having the major axis in the Y axis direction is formed on the portion in which the laser light L0 of the inspection surface 210 is entered. When the defects such as the adhesion of scratches and foreign matters are not existed on the irradiation area 220, the remaining light L1 except the light which is absorbed by the irradiation area 220 is emitted in the Y axis positive direction at the reflection angle (90°−α) of the same angle with the incident angle (90°−α) as the regular reflection light.

Therefore, the light does not essentially emit to the direction to which the regular reflection light L1 is emitted.

On the other hand, when the scratch is existed on the irradiation area 220, the laser beam L0 is reflected diffusely by a microscopic asperity and the like forming the scratch, so that the scattered light is generated by the diffuse reflection other than the regular reflection light L1.

When the foreign matter is adhered to the irradiation surface 220, the laser beam L0 is reflected diffusely by the convex wall of the foreign matter and so on, so that the scattered light is caused by the diffuse reflection other than the regular reflection light L1.

Accordingly, the L2 which is a part of the scattered light (hereinafter referred to as scattered light) generated by the existence of the defect such as the scratch and the foreign matter is substantially orthogonal to the Y axis, and is entered to the scattered light detecting optical system 40 having the optical axis O2 directed to the irradiation area 220 at a depression angle β with respect to the inspection surface.

On the contrary, if the laser beam L0 is emitted from the LD10, the turning stage 31 comprising the scanning device 30 is turned in the direction arrow R at a constant angular velocity, and the turning stage 31 is displaced in the arrow direction (Y axis positive direction) at a constant velocity by the liner motor 32.

Figures 2A, 2B:
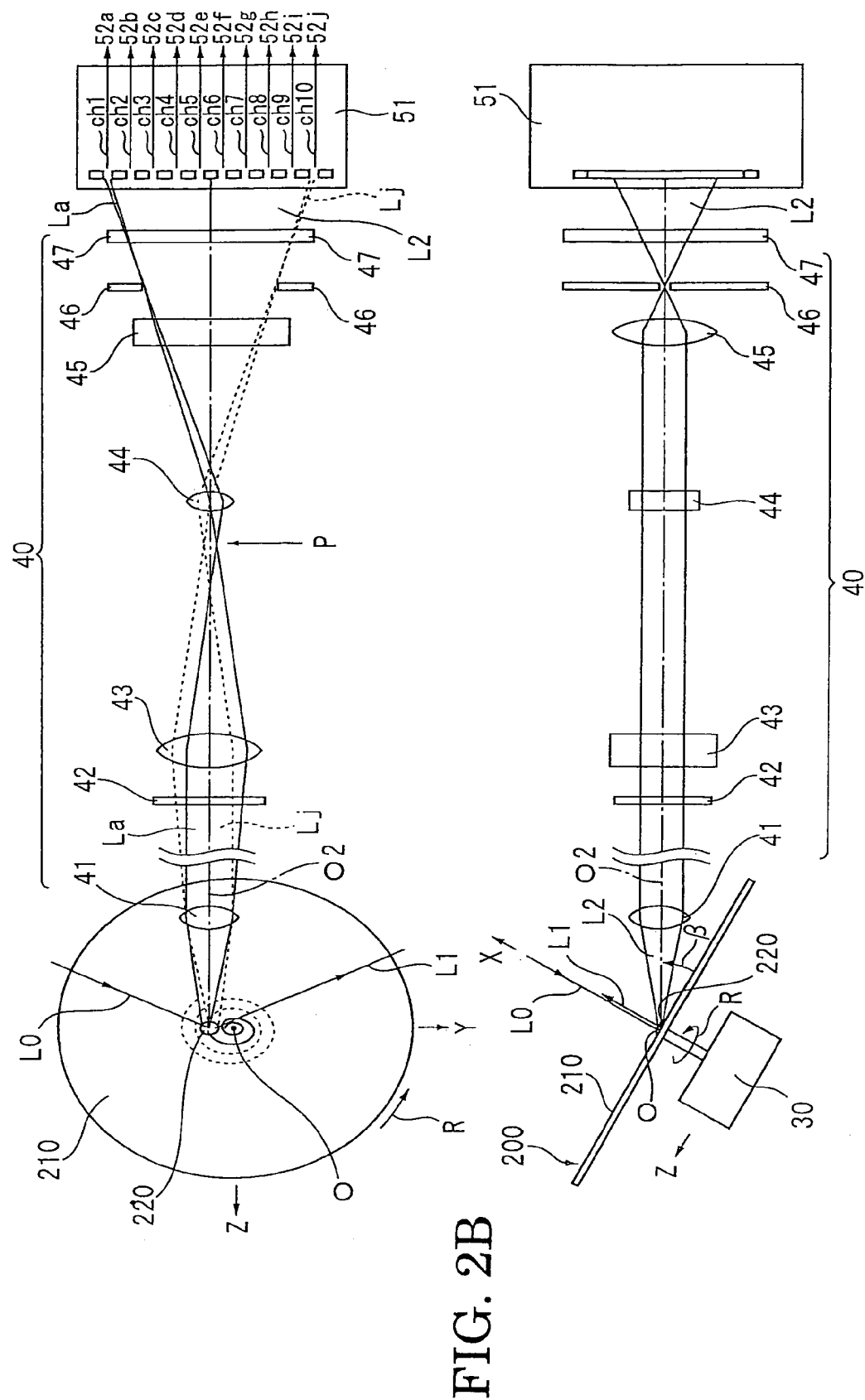
FIG. 2A is a plan view mainly illustrating a scattered light detecting optical system and a light intensity detecting device in the surface inspection apparatus shown in FIG. 1.
FIG. 2B is a side view illustrating the same scattered light detecting optical system and light intensity detecting device.

Therefore, the irradiation area 220 on the inspection surface 210 of the wafer 200 provided on the turning stage 31 relatively moves in spiral on the inspection surface 210 as shown in FIG. 2A. As a result, the laser beam L0 scans the inspection surface 210 in spiral.

The width of pitch of the scanning locus in the radial direction of the wafer 200 can be adjusted by adjusting at least any one of the turning angle velocity of the turning stage 31 or the displacement velocity of the liner motor 32. The laser beam L0 can scan the entire inspection surface 210 by adjusting the pitch of the scanning locus while adjusting the size of the irradiation area 220.

When the defect is existed on the irradiation area 220 and the scattered light L2 caused by the defect is condensed by the condenser lens 41 of the scattered light detecting optical system 40, and the wave surface of the scattered light L2 is adjusted by the polarizing plate 42. After that the scattered light L2 is entered to the cylindrical lenses 43, 44, 45, and incident of light (including backlight) except from the irradiation area 220 is eliminated by the filed stop 46, and is reduced by the ND filter 47, and then entered to the multianode PMT51.

In this embodiment, in order to simplify the explanation, the entire irradiation area 220 where the laser beam L0 is entered onto the inspection surface is adopted as a detecting object of the scattered light. However, the peripheral area of the irradiation area 220 where the irradiation intensity of the laser beam L0 is relatively small may be excluded from the detecting object of the scattered light because the intensity level of the detecting scattered light is low. In this case, the scattered light from the excluded area (peripheral area) is shielded by the field stop 46 in order to prevent the incidence into the mutianode PMT51.

Since the inclined plane of the scattered light L2 is divided into the ten light intensity detecting areas such as ch1 to ch10 in the Y axis direction, i.e. major axis direction of the irradiation area 220, the multianode PMT51 spatially decomposes the scattered light L2 emitted from the irradiation area 220 in the major axis direction (Y axis direction).

Accordingly, as illustrated in FIG. 3, the ch1 of the multianode PMT 51 detects the light intensity of the scattered light La emitted from the area 220a, which is positioned in the vicinity of the longest diameter of the Y axis negative direction in the major axis direction of the irradiation area 220, from the scattered light L2 emitted from the irradiation area 220. The ch2, correspondingly, detects the light intensity of the scattered light Lb emitted from the area 220b adjacent to the area 220a from the scattered light L2 emitted from the irradiation area 220, and the ch10 detects the light intensity of the scattered light Lj emitted from the area 220j, which is positioned in the vicinity of the longest diameter of the Y axis positive direction, from the scattered light L2 emitted from the irradiation area 220.

The light intensity of the scattered light La to Lj respectively detected corresponding to each area 220a to 220j of the irradiation area 220 by each ch1 to ch10 of the multianode PMT51 is output as a predetermined electric signal after photoelectric conversion. Those output signals are respectively input to each amplifier 52, and then the signals are amplified by the each amplifier 52 provided in accordance with the each channel of ch1 to ch10. The signal amplified by each amplifier 52 is input to each PBF 53, and a predetermined noise component is respectively cut by the corresponding BPF 53. After that each signal is input to the A/D converter 54, and is digitized, and then the each digitized signal is stored in the corresponding memory 55.

The digital signal displaying each intensity V of the scattered light of La to Lj stored in each memory 55 is analyzed by the analysis device 56. With this analysis device 56, if the scratch formed through a number of areas on the irradiation area 220 is existed as shown in FIG. 4A, each intensity V of the scattered light La to Lj respectively read from the memory 55 corresponding to each channel is recognized as a positive output V continued between a number of channels as illustrated in FIG. 4D.

On the other hand, as shown in FIG. 4C, if the foreign matters are dotted with some areas in the irradiation area 220, the intensity V of the scattered light La to Lj respectively read from the memory 55 corresponding to each channel is recognized as positive outputs V in a plurality of channels, but the channels including the positive outputs are not continued, and they are separated, as shown in FIG. 4F.

When the light intensity V of a predetermined level or higher is detected by a channel, and the light intensity of the substantially same level is detected in the channels adjacent to the channel, and then a number of channels by which such light intensity V is detected is continued (FIG. 4D), the light intensity V can be analyzed and determined that a large defect (such as a scratch) extending in the Y axis direction in the irradiation area 220 corresponding to the arrangement direction (Y axis direction) of the channel is presented. On the other hand, although the light intensity V of a predetermined level or higher is detected by a channel, if the light intensity V detected in the channels adjacent to the channel is light intensity V indicating a significant difference from a predetermined level (FIG. 4F), or although the light intensity V of the substantially same level is detected in adjacent channels, if the channels detected such light intensity V are continued only for 2 or 3 channels (FIG. 4E), the defect is not a defect continued in a predetermined direction within the irradiation area, and the defect is analyzed and determined as a small defect (such as adhesion of a foreign matter) illustrated in FIG. 4C and FIG. 4B.

As a result, a plurality of small defects and a single large defect, which were difficult to be identified, can be easily identified.

Moreover, the existence position of the defect in the irradiation area 220 can be preciously detected at least in the arrangement direction of the channel.

Further, when the defect is distinguished between the formed scratch and the adhered foreign matter, the scratch is formed relatively longer than the foreign matter, and the foreign matter has the small size in many cases, so that the scratch and the foreign matter can also be distinguished depending upon the length of the size.

As shown in FIG. 4D, when the light intensity V is detected continuous to a number of channels, the light intensity V can be determined as a long size defect, i.e. a scratch. At the same time, as shown in FIGS. 4E, 4F, when the light intensity V is detected continuous to the adjacent two or three channels, or when the light intensity V is detected in a single channel, the light intensity V can be determined as a short size defect, i.e. a foreign matter.

By increasing the sampling frequency by the A/D converter, the output of each channel can be detected by time division, so that the length (width) of the defect along the arrow R direction in the irradiation area 220 can detected in some measure.

As described above, the Y axis direction of the irradiation area 220 is spatially decomposed, and the R direction orthogonal to the Y axis is divided in a time, so that the scattered light intensity can be detected by dividing the irradiation area 220 into a two-dimensional matrix, and the identification performance for a defect type can be further improved while improving the resolution.

Instead of using the time division, a multianode PMT51 for detecting the entered light by spatially decomposing into the two-dimensional matrix is applied as the multianode PMT 51 while increasing the imaging magnification in the vertical direction of the scattered light detecting optical system 40 as well as the Y axis direction.

The crosstalk among the individual scattered light spatially decomposed by the multianode PMT51 can be effectively prevented and controlled by setting the reflecting power in the direction to which the scattered light is spatially decomposed, i.e. the Y axis direction larger in the positive direction than the reflecting power in the vertical direction, with the three cylindrical lenses 42, 43, and 44.

MODIFICATION EXAMPLE 1

Figure 5A:
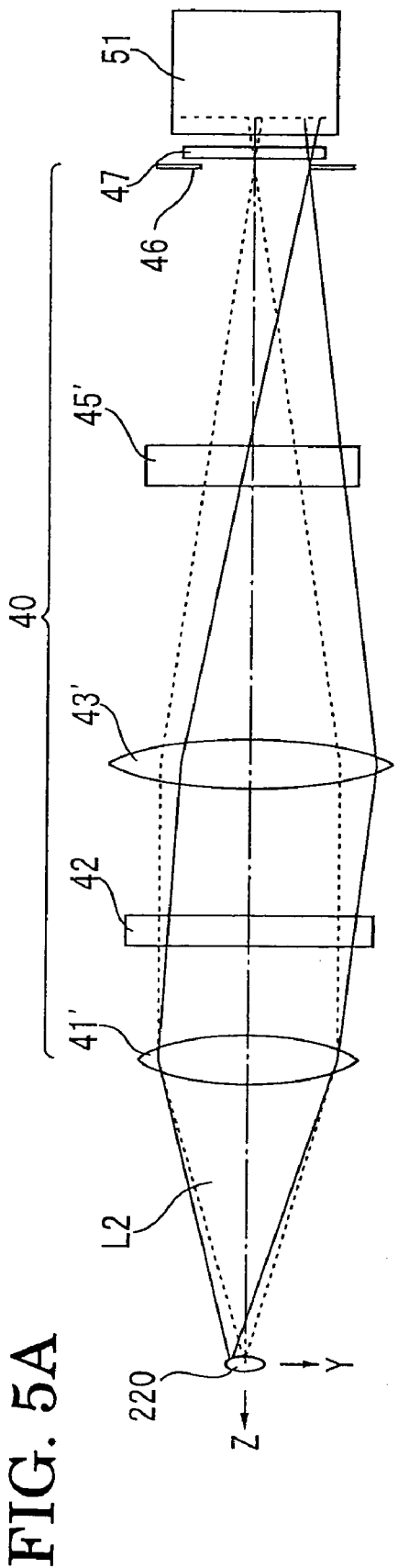
FIGS. 5A, 5B illustrate another embodiment (modification example 1) of the scattered light detecting optical system.
Figure 5B:
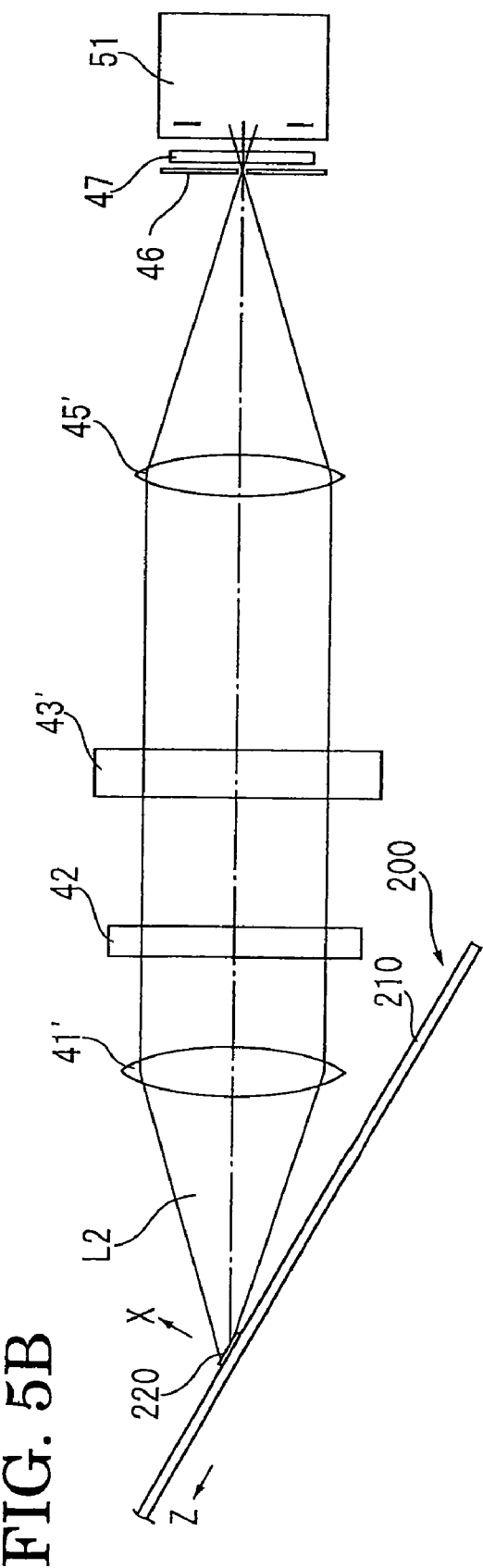

FIG. 5 illustrates the modification example 1 of the scattered light detecting optical system 40 in the surface inspection apparatus 100 shown in FIG. 1, and shows a scattered light detecting optical system 40 used for a surface inspection apparatus 100 other than the scattered light detecting optical system 40 using the telecentric optical system shown in FIG. 2.

In the scattered light detecting optical system 40, the imaging surface is existed in a predetermined plane perpendicular to the optical axis, and the field stop is easily placed in this predetermined plane. The scattered light detecting optical system 40 comprises a condenser lens 41', a polarizing plate 42, cylindrical lenses 43', 45', a field stop 46, and an ND filter 47.

The surface inspection apparatus 100 using the above constructed scattered light detecting optical system 40 can perform the same function and the same effect with the surface inspection apparatus 100 according to the above described first embodiment.

MODIFICATION EXAMPLE 2

FIG. 6 shows the modification example 2 of the scattered light detecting optical system 40 in the surface inspection apparatus 100 illustrated in FIG. 1, and illustrates a scattered light detecting optical system 40 used in a surface inspection apparatus 100, other than the scattered light detecting optical system 40 using the telecentric optical system shown in FIG. 2.

The scattered light detecting optical system 40 is a most simple structure of an asymmetric optical system, and comprises a condenser lens (spherical lens) 41", a polarizing plate 42, a cylindrical lens 43", and an ND filter 47.

The same function and the same effect with the surface inspection apparatus 100 according to the above described first embodiment can be carried out by using the surface inspection apparatus 100 to which the above constructed scattered light detecting optical system 40 is applied.

Second Embodiment

Figure 7:
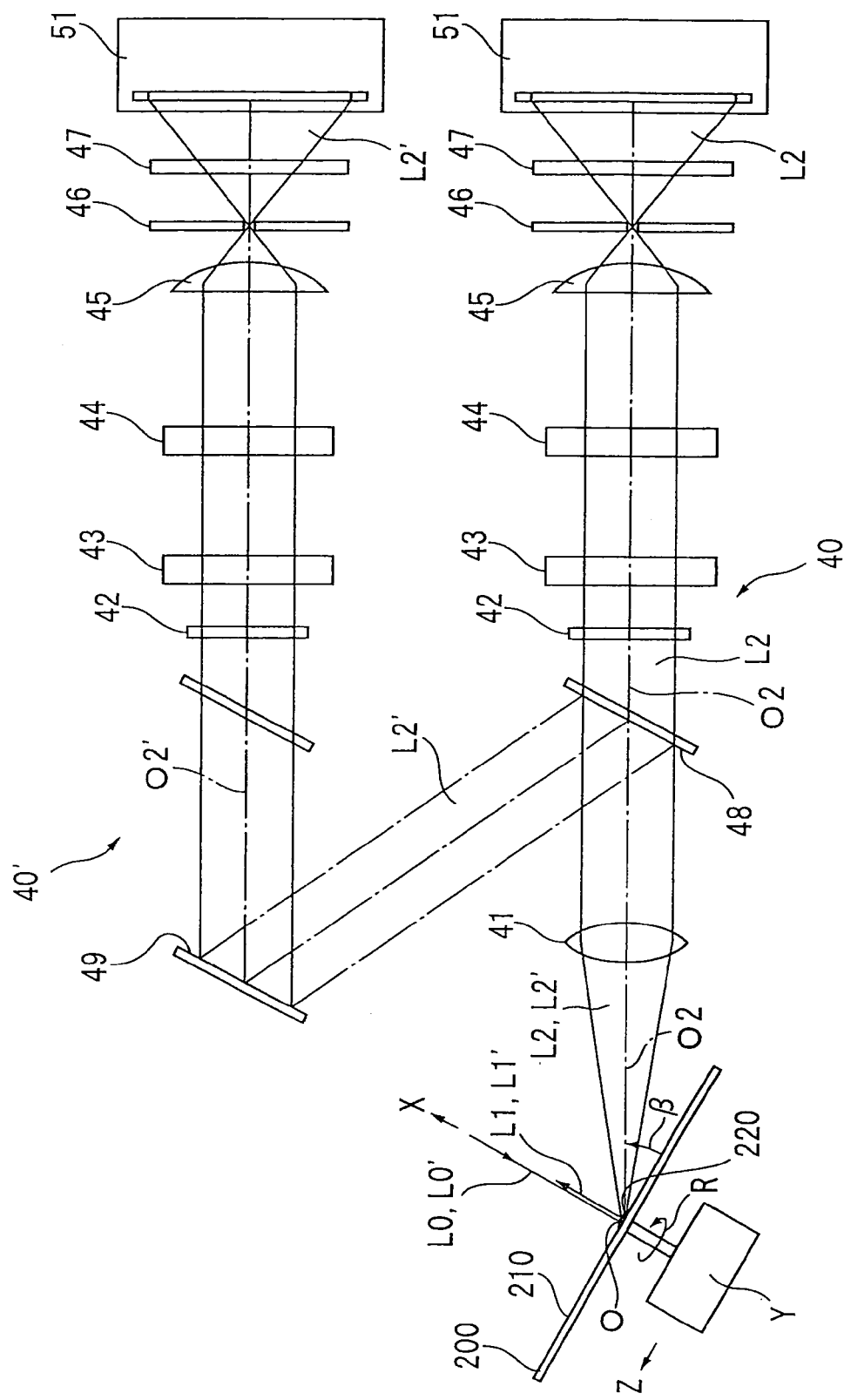
FIG. 7 shows a side view mainly showing a scattered light detecting optical system and a light intensity detecting device in a surface inspection apparatus according to an embodiment in which a scattered light for each wavelength is detected by entering laser beams of two wavelengths on an inspection surface.

In the above described first embodiment, FIG. 7 illustrates a structure that the LD10 and the irradiation optical system 20 are set to irradiate two laser beams having different wavelength $\lambda$ each other onto the same portion (irradiation area) 220 of the inspection surface 210 of the wafer 200. FIG. 7 also illustrates the structure comprising two scattered light detecting optical systems 40, 40' and two light intensity detecting devices 50, 50' so as to respectively condense the scattered light L2 of the wavelength $\lambda 1$ and the scattered light L2' of the wavelength $\lambda 2$ emitted from the irradiation area 220 and to detect by spatially decomposing each of the scattered light L1, L'.

Here, the two scattered light detecting optical systems 40, 40' uses a common condenser lens 41. In the two scattered light detecting optical systems 40, 40', a dichroic mirror is for transmitting the scattered light L2 of the wavelength $\lambda 1$ and for reflecting the scattered light L2' of the wavelength $\lambda 2$ onto the optical path of the scattered light L2, L2' is disposed between the condenser lens 41 and the polarizing plate 41 of the scattered light detecting optical system 40. A mirror 49 for reflecting the scattered light L2' of the wavelength $\lambda 2$ reflected by the dichroic mirror 48 is arranged between the dichroic mirror 48 and the polarizing plate 42 of the scattered light detecting optical system 40', and also onto the optical path of the reflected light by the dichroic mirror 48.

The structure of the downstream side in the advancing direction of the scattered light L2 after the polarizing plate 42 in the scattered light detecting optical system 40 and the structure of the downstream side in the advancing direction of the scattered light L2' after the polarizing plate 42 in the scattered light detecting optical system 40' are essentially the same as the structure of the downstream side in the advancing direction of the scattered light L2 after the polarizing plate 42 in the scattered light detecting optical system 40 in the first embodiment.

However, it is obvious that the distances, etc. between the lenses are appropriately set to obtain an appropriate imaging in accordance with the wavelengths $\lambda 1$, $\lambda 2$ of the scattered light L2, L2'.

According to the surface inspection apparatus according to the above constructed embodiment, other than the function and the effect by the first embodiment, when the defect formed on the inspection surface 210 generates the scattered light L2, L2' with respect to the wavelength λ1 or the wavelength λ2, each scattered light L2, L2' of each wavelength λ1, λ2 can be detected separately, so that the analysis accuracy when analyzing a position, size, and type of the defect based on the defected result can be further improved.

In the two scattered light detecting optical systems 40, 40', a part of the optical path of the scattered light L2 and the optical path of the scattered light L2' is shared by using the common condenser lens 41. However, the present invention is not limited to this embodiment, and completely separated two scattered light detecting optical systems 40, 40' may be used.

The irradiation area 220 on the inspection surface 210 may be formed in different positions depending upon the incident laser beams L0, L0'.

The laser beams L0, L0' are emitted from the two separate LD10, but a single light source emitting a broad luminous flux including the two wavelengths λ1, λ2 can be used other than these laser beams.

In this case, the irradiation optical systems are completely shared, so that the irradiation system is constructed by a single light source and a single irradiation optical system. The manufacturing cost of the surface inspection apparatus and the task for adjusting the optical axis can be reduced, and the reliability of the apparatus can be improved, as a result.

In each of the above described embodiments, the linear motor 32 displaces the wafer 200 along the Y axis direction by a constant velocity, so the major axis direction of the irradiation area 220 is along a normal direction of the scanning locus spiral. However, the surface inspection method and the surface inspection apparatus of the present invention are not limited to the embodiments.

That is, the irradiation optical system 20 is arranged such that the irradiation area 220 is formed onto the Z axis of the inspection surface 210 and the liner motor displaces the wafer 200 along the Z axis direction by a constant velocity. In this case, the major axis direction of the irradiation area 220 is along the tangent direction of the scanning locus spiral.

In each of the embodiments, the scanning locus formed onto the inspection surface 210 of the wafer 200 is a spiral toward the outer circumference edge side from the center O side of the wafer 200. However, the scanning locus may be a spiral toward the center O side from the outer circumference edge side of the wafer 200 by setting the initial position of the irradiation area 220 on the inspection surface 210 to the outer circumference edge side of the wafer 200. The same function and effect with the above described embodiments can be obtained by using such the embodiment.

Moreover, the scanning locus by the scanning device 30 is not limited to the spiral as each of the described embodiments; the scanning locus may be a concentric circle shape, for example. That is, the scanning locus may be formed by a sequential track scanning such as scanning the next concentric circle by moving radially after the scanning of one concentric circle is completed.

It is obvious that the scanning locus is simply formed in zigzag, but the scanning device 30 in the above embodiments capable of forming the smooth spiral shaped scanning locus hardly have the influence of the inertia force of the scanning object (wafer 200), so that the reliability of the surface inspection apparatus 100 can be improved.

In each of the above embodiments, the light intensity is detected by spatially decomposing the scattered light from the elliptical shaped irradiation area 220 in the major axis direction. However, in the surface inspection method and the surface inspection apparatus of the present invention, the light intensity may be detected by spatially decomposing in the minor axis direction of the elliptical shape or in an oblique direction with respect to the minor axis direction of the elliptical shape (direction forming an angle except 0 degree with respect to the minor axis direction). The elliptical shaped irradiation area may also be adopted as a substantially true circular shape. In this case, the reflective power in the direction orthogonal to the inspection surface and the reflective power in the direction parallel to the inspection surface by the irradiation optical system are respectively set in accordance with the incident angle (or depression angle) to the inspection surface.

As described above, according to the surface inspection method of the present invention, it is possible to distinguish between a plurality of separated small defects and a consecutive large defect by sequentially comparing each of detecting intensity by a plurality of channels arranged in the one-dimensional direction between adjacent channels.

It is also possible to distinguish between adhesion of a plurality of small defects (projections with respect to a surface) and a long scratch (a concave with respect to surface) which were difficult to distinguish.

According to the surface inspection method according to the present invention, the one-dimensional direction to be decomposed into a plurality of channels corresponds to the major axis direction of the spot of the incidence luminous flux in the inspection surface, so that the resolution of the emitting position of the scattered light in the major axis direction of the spot can be further improved.

By improving the resolution in the major axis direction of the spot, the detecting pitch on the spot can be set longer compared to the case for improving the resolution in the minor axis direction of the spot. Therefore, it is possible to facilitate preventing crosstalk between adjacent channels.

According to the surface inspection method of the present invention, the one-dimensional direction to be decomposed into a plurality of channels corresponds to a predetermined angular direction with respect to the minor axis direction of the spot of the incidence luminous flux on the inspection surface; therefore, the resolution of the emitting position of the scattered light can be further improved in a predetermined angular direction of the spot.

According to the surface inspection method of the present invention, with the assumption that the defect formed on the inspection surface is the defect distinctively generating the scattered light with respect to a predetermined wavelength, the luminous flux to be irradiated onto the inspection surface is adopted as light having different wavelengths each other more than 1 or a broad single light including the wavelengths more than 1, and the scattered light of each wavelength is separately detected, so that analysis accuracy when analyzing a position, size, or type of the defect based on the detected result can be improved.

According to the surface inspection apparatus of the present invention, it is possible to distinguish between a plurality of separated small defects and a consecutive large defect by sequentially comparing each of detecting intensity by a plurality of channels arranged in the one-dimensional direction between adjacent channels.

It is also possible to distinguish between adhesion of a plurality of small defects (projections with respect to a surface) and a long scratch (a concave with respect to surface) which were difficult to distinguish.

According to the surface inspection apparatus of the present invention, when the light intensity detecting device is set to decompose the scattered light in to a plurality of channels and in the one-dimensional direction, and to detect the light intensity, the reflecting power in the one-dimensional direction of the scattered light detecting optical system is set larger than the reflecting power in the orthogonal direction. Accordingly, crosstalk that the scattered light to be entered to adjacent channels is entered to the each channel can be controlled and the detecting accuracy is improved.

According to the surface inspection apparatus of the present invention, the scattered light detecting optical system comprises the cylindrical lens having the reflecting power in the one-dimensional direction and without having the reflecting power in the orthogonal direction. The reflecting power of the one-dimensional direction can accordingly be set larger than the reflecting power of the orthogonal direction by the simple structure.

According to the surface inspection apparatus of the present invention, when the conjugate position in the direction orthogonal each other is set in the substantially same position in the optical axis direction. Therefore, an effective field stop can be set by setting the field stop in the conjugate position when the field stop is set in the scattered light detecting optical system.

According to the surface inspection apparatus of the present invention, the one-dimensional direction in the inclined plane in the light intensity detecting device corresponds to the major axis direction of the spot of the incidence luminous flux in the inspection surface, so that the resolution of the emitting position of the scattered light in the major axis direction of the spot can be improved.

By improving the resolution in the major axis direction of the spot, the detecting pitch on the spot can be set longer compared to the case for improving the resolution in the minor axis direction of the spot. Therefore, it is possible to facilitate preventing crosstalk between adjacent channels.

According to the surface inspection apparatus of the present invention, the one-dimensional direction on the inclined plane of the light intensity detecting device corresponds to a predetermined angular direction with respect to the minor axis direction of the spot of the incidence luminous flux on the inspection surface; therefore, the resolution of the emitting position of the scattered light in a predetermined angular direction of the spot can be improved.

According to the surface inspection apparatus of the present invention, the scanning device which makes the scanning locus in a smooth spiral can be configured by the simple combination such as the turning device and the linear movement device.

The scanning of the smooth spiral hardly has the influence of the inertial force of the scanning object compared to the scanning device for carrying out the sequential track scanning which concentrically scans a track, for example, then scans a next track by moving radially when the scanning of the one track is completed.

According to the surface inspection device of the present invention, with the assumption that the defect formed on the inspection surface is the defect distinctively generating the scattered light with respect to a predetermined wavelength, in the surface inspection device to be set that the luminous flux to be irradiated on the inspection surface is adopted as the light more than 1 having different wavelengths each other, or the broad single light including the wavelengths more than 1, the above described scattered light detecting optical system and the light intensity detecting device are equipped in accordance with the number of light of the wavelengths more than 1, so that the scattered light of each wavelength can be respectively detected, so that the analysis accuracy when analyzing a position, size, and type of the defect based on the detected results can be improved.

What is claimed is:

1. A surface inspection method, comprising:
    irradiating a predetermined luminous flux with respect to an inspection surface of an inspection object as an object of the surface inspection at a predetermined incident angle;
    relatively displacing at least one of said luminous flux and said inspection object such that said luminous flux scans said inspection surface;
    reflecting the luminous flux at a portion of said inspection surface at which said luminous flux has been irradiated;
    spatially decomposing a scattered light reflected at said portion of said inspection surface into a plurality of channels which is arranged at least in a one-dimensional direction along a direction orthogonal to a scanning direction of said luminous flux;
    detecting in each of the channels a light intensity of each of scattered lights which is obtained by decomposing said scattered light; and
    determining a size along said one-dimensional direction of a defect on the inspection surface by comparing the light intensity detected in each of the channels between the channels adjacent to each other; and outputting the information to a display device.

2. The surface inspection method according to claim 1, wherein a spot of an incident luminous flux as said portion of said inspection surface at which said luminous flux has been irradiated comprises an elliptical shape, and said one-dimensional direction is a direction corresponding to a major axis direction of said spot.

3. The surface inspection method according to claim 1, wherein a spot of an incident luminous flux as the portion of the inspection surface at which the luminous flux has been irradiated comprises an elliptical shape, and said one-dimensional direction is a direction corresponding to a predetermined angular direction with respect to a minor axis direction of said spot.

4. The surface inspection method according to claim 1, further comprising:
    converging and detecting at least two scattered lights having wavelengths different from each other reflected from the portion of said inspection surface, respectively, by means of irradiating the luminous flux having at least two different wavelengths to the portion of the inspection surface;
    spatially decomposing the scattered lights having the wavelengths different from each other into a plurality of channels, respectively; and
    detecting the light intensity of each of decomposed scattered lights which is obtained by decomposing said scattered lights.

5. A surface inspection apparatus, comprising:
    a light source for emitting a predetermined luminous flux;
    an irradiation optical system for irradiating the luminous flux emitted from said light source with respect to an inspection surface of an inspection object as an object of a surface inspection at a predetermined incident angle;
    a scanning device configured to relatively displace at least one of said luminous flux and said inspection object such that said luminous flux scans said inspection surface;
    a light intensity detecting device configured to detect an intensity of an incident light; and a scattered light detecting optical system for guiding a scattered light emitted from a portion of said inspection surface at which said luminous flux has been irradiated, wherein said light intensity detecting device is set to spatially decompose said scattered light into a plurality of channels, which is arranged at least in a one-dimension direction along a direction orthogonal to a scanning direction of said luminous flux, and to detect in each of the channels the light intensity of each of scattered lights which is obtained by decomposing the scattered light, and said light intensity detecting device is set to determine a size along said one-dimensional direction of a defect on the inspection surface by comparing the light intensity detected in each of the channels between the channels adjacent to each other.

6. The surface inspection apparatus according to claim 5, wherein said scattered light detecting optical system is set such that a reflecting power in said one-dimensional direction is larger than a reflecting power in a direction orthogonal to the one-dimensional direction.

7. The surface inspection apparatus according to claim 6, wherein said scattered light detecting optical system comprises a cylindrical lens having the reflecting power in said one-dimensional direction and without having the reflecting power in said direction orthogonal to the one-dimensional direction.

8. The surface inspection apparatus according to claim 5, wherein said scattered light detecting optical system is set such that a conjugate position in said one-dimensional direction and a conjugate position in said direction orthogonal to the one-dimensional direction are a substantially same position in an optical axis direction.

9. The surface inspection apparatus according to claim 5, wherein a spot of an incident luminous flux as said portion of said inspection surface at which said luminous flux has been irradiated comprises an elliutical shape, and said one-dimensional direction is a direction corresponding to a major axis direction of the spot.

10. The surface inspection apparatus according to claim 5, wherein a spot of an incident luminous flux as said portion of said inspection surface at which said luminous flux has been irradiated comprises an elliptical shape, and said one-dimensional direction is a direction corresponding to a predetermined angular direction with respect to a minor axis direction of the spot.

11. The surface inspection apparatus according to claim 5, wherein said inspection surface is a substantially true circle, and said scanning device comprises a turning device for turning said inspection object about a center of the substantially true circle as a turning center and a linear movement device for linearly moving the inspection object in a predetermined direction along said inspection surface, and a locus by said scanning is a spiral shape.

12. The surface inspection apparatus according to claim 5, wherein said light source comprises at least two light sources for emitting luminous fluxes having wavelengths different from each other, or a light source for emitting a broad luminous flux including wavelengths different from each other, and said scattered light detecting optical system and said light intensity detecting device comprise at least two scattered light detecting optical systems and at least two light intensity detecting devices, so as to converge and detect at least two scattered lights emitted from the portion of said inspection surface.

* * * * *